United States Patent [19]

Christensen et al.

[11] Patent Number: 4,617,152

[45] Date of Patent: Oct. 14, 1986

[54] β-LACTAMS CONTAINING AN α-EXOCYCLIC DOUBLE BOND

[75] Inventors: Burton G. Christensen, Cliffside Park; Lovji D. Cama, Cresskill; Susan M. Schmitt, Scotch Plains, all of N.J.

[73] Assignee: Merck & Co., Inc., Rahway, N.J.

[21] Appl. No.: 703,056

[22] Filed: Feb. 19, 1985

[51] Int. Cl.$^4$ .................. C07D 498/04; C07F 7/10
[52] U.S. Cl. ...................... 540/200; 540/300; 544/69; 544/71; 544/90
[58] Field of Search .................. 544/69, 71, 90; 260/239 A, 245.2 R

[56] References Cited

U.S. PATENT DOCUMENTS

| | | | |
|---|---|---|---|
| 4,206,219 | 6/1980 | Christensen et al. | 514/210 |
| 4,234,596 | 11/1980 | Christensen et al. | 514/210 |
| 4,309,346 | 1/1982 | Christensen et al. | 260/239 A |
| 4,383,946 | 5/1983 | Christensen et al. | 260/245.2 T |
| 4,521,337 | 6/1985 | Southgate et al. | 544/90 X |

FOREIGN PATENT DOCUMENTS 67517 12/1982 European Pat. Off. .

OTHER PUBLICATIONS

Heterocycles, 1984, vol. 21, pp. 29–40, by D. H. Shih, et al.
Reagents for Organic Synthesis, vol. 1, pp. 723–729, by S. L. Feiser (1967) John Wiley and Sons, Inc., New York.

*Primary Examiner*—Richard L. Raymond
*Attorney, Agent, or Firm*—Robert J. North; Hesna J. Pfeiffer

[57] ABSTRACT

A process is described for selectively obtaining 1-β-methylcarbapenem intermediates. The desired chirality is obtained through the hydrogenation of certain bicyclic β-lactam ring structures containing an exocyclic methylene double bond alpha to the β-lactam ring, in the presence of a Group VIII metal hydrogenation catalyst. The hydrogenation results in a mixture of α- and β-methyl epimers having a high β/α epimeric ratio. New 1-β-methylcarbapenem intermediates made by the process are also described.

6 Claims, No Drawings

β-LACTAMS CONTAINING AN α-EXOCYCLIC DOUBLE BOND

BACKGROUND OF THE INVENTION

This invention relates to a chiral process for selectively obtaining high yields of 1-β-methylcarbapenem intermediates for the subsequent synthesis of 1-β-methylcarbapenem antibiotics. The process involves introducing an exocyclic α-methylene double bond into a bicyclic β-lactam ring structure and then subjecting the compound to hydrogenation conditions with a Group VIII transition metal hydrogenation catalyst which preferentially results in the formation of the 1-β-methylcarbapenem intermediates.

1-β-Methylcarbapenems, as described in the reference *Heterocycles*, 1984, Vol. 21, pp. 29-40 by D. H. Shih, F. Baker, L. Cama and B. G. Christensen, are extremely useful and effective broad spectrum antibiotics, useful against a wide variety of bacteria including Gram-positive bacteria including *S. aureus*, Strep. sp., *B. subtilis*, and Gram-negative bacteria such as *E. coli*, Shigella sp., Enterobacter sp., Klebsiella sp., Proteus, Serratia and Pseudomonas sp.

A method of synthesizing 1-β-methylcarbapenems is described in the above-cited reference in which the beta-methyl chirality is introduced into the molecule by base-catalyzed alkylation producing a mixture of α and β epimers which are separated by chromatographic procedures.

However, because of the relatively low β/α epimeric ratio obtained by this alkylation route, newer methods for obtaining the desired β-methyl epimer intermediate on a larger scale are constantly being sought.

SUMMARY OF THE INVENTION

It has been found that by introducing an exocyclic α-methylene double bond into the secondary ring of a bicyclic β-lactam ring system, and then subjecting said compound to hydrogenation conditions utilizing a Group VIII transition metal hydrogenation catalyst, the stereochemistry of the molecule enables the hydrogenation to proceed stereoselectively to produce the β-methyl isomer in a β/α epimer ratio greater than 1 and as high as 9:1.

In accordance with this invention there is provided a process for stereoselectively reducing an exocyclic methylene double bond in a bicyclic compound of the structural formula (I):

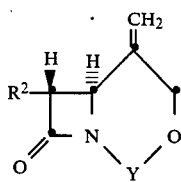

where $R^2$ is independently H, linear or branched $C_1$-$C_3$ alkyl, which can be substituted with fluoro or hydroxy, and Y is a divalent bridging-protecting group, derived from a ketone, aldehyde or organosilicon compound, said group being stable to catalytic hydrogenation and removable by acid or base hydrolysis, said process comprising the step of contacting said compound with a hydrogen atmosphere in the presence of a supported or unsupported Group VIII transition metal hydrogenation catalyst and in the presence of a solvent for said bicyclic compound, at a temperature below the boiling point of the solvent, for a sufficient time to yield a mixture of α- and β-methyl epimers having a β/α molar ratio of greater than 1.

The process is illustrated by the following flow diagram:

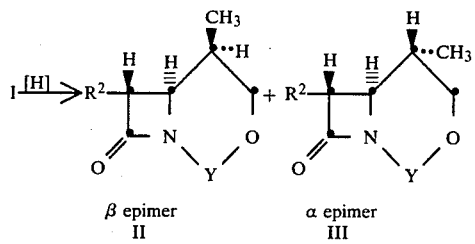

β epimer II    α epimer III

Further provided is a composition of the following structural formula, being an intermediate useful in producing compositions of above-described structure (I):

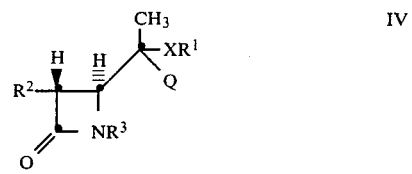

wherein $R^2$ is independently selected from hydrogen, linear or branched $C_1$-$C_3$ alkyl, which can be substituted with fluoro, hydroxy, or protected hydroxy, $R^3$ is hydrogen or a protecting group, X is sulfur or selenium, Q is hydroxymethyl, carboxy or $C_1$-$C_4$ alkoxycarbonyl, and $R^1$ is $C_1$-$C_4$ alkyl, $C_6$-$C_{10}$ aryl, heteroaryl, which can contain substituents inert under the reaction conditions of forming structures I or IV, and include $C_1$-$C_4$ alkyl, alkoxy, nitro and the like.

Furthermore, there is provided a composition of the following structural formula, an intermediate formed from the oxidation of structure IV and, useful in producing composition (I):

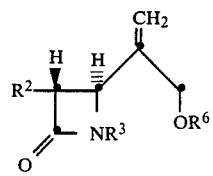

wherein $R^2$ is independently selected from hydrogen, linear or branched $C_1$-$C_3$ alkyl, which can be substituted with fluoro, hydroxy, or protected hydroxy, $R^3$ is hydrogen or a protecting group, $R^6$ is hydrogen, a protecting group, or a covalent bond, and where $R^6$ is a covalent bond, $R^3$ and $R^6$ are joined to form Y, a divalent bridging-protecting group derived from a ketone, aldehyde or organosilicon compound, said group being stable to catalytic hydrogenation and removable by acid or base hydrolysis. As described above, where $R^3$ and $R^6$ join to form Y, structure I results.

DESCRIPTION OF THE INVENTION AND THE PREFERRED EMBODIMENTS

The basic invention process is best illustrated by reference to the above diagram depicting the hydrogenation of structure I.

As is seen, the α-exocyclic methylene double bond of I is hydrogenated to produce the β-methyl epimer II and the α-methyl epimer III. The hydrogenation conditions employed are conventional in the art, and it was found surprisingly that the hydrogenation of structure I, particularly where $R^2$ is

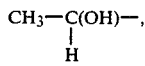

gave rise selectively to the β-methyl epimer in the resulting product mixture which contained a β/α epimer molar ratio of greater than 1.

The catalyst employed in the hydrogenation is a conventional Group VIII transition metal hydrogenation catalyst typically used for olefins which can be soluble or insoluble in the reaction medium, but wherein said catalyst is generally not effective for causing hydrogenation of the bicyclic beta-lactam ring structure under the hydrogenation conditions. Preferred metals in the catalyst are nickel, palladium, platinum, rhodium, and the metal in the catalyst can be in the form of free metal, salts or compounds thereof. The catalysts can be used in the bulk and unsupported form, e.g. palladium hydroxide, or in the supported form on a suitable substrate, e.g. activated carbon, inorganic sulfate or carbonate, said substrate not intervening in the hydrogenation process. Representative examples of Group VIII transition metal hydrogenation catalysts which can be used include palladium hydroxide, platinum oxide, platinum black, platinum-on-carbon, palladium-on-carbon, colloidal palladium or platinum, platinum or palladium on barium sulfate or barium carbonate, Raney nickel, i.e. W-2, W-4, W-6, or other grades as prepared by conventional procedures, soluble rhodium catalysts including tris(triphenylphosphine)chlororhodium, and the like. The catalyst can be soluble in the solvent used, such as the triphenylphosphine rhodium compound, or insoluble, such as the heterogeneous catalysts, eg. Raney Nickel. A preferred catalyst for use in the process is Raney Nickel as produced by the conventional process described in the reference L. F. Feiser, "Reagents for Organic Synthesis", Vol. 1, p. 723 (John Wiley & Sons, New York), incorporated by reference herein for that purpose. Catalysts operable in the process are produced by conventional procedures.

Solvents for Structure I which can be used for the hydrogenation of I in the process should be inert under the reaction conditions and have a boiling point in the temperature range of about 50°-100° C. for adequate temperature to be achieved during the process. Representative examples of solvents which can be used in the process include protic and aprotic liquids such as $C_1$-$C_3$ alcohols, $C_3$-$C_6$ alkyl carboxylic esters, $C_4$ cyclic mono- and diethers, and derivatives thereof, which can contain substituents such as lower alkyl and alkoxy, inert under the hydrogenation conditions. Representative examples include EtOH, MeOH, MeOAc, EtOAc, dioxane, tetrahydrofuran and the like. A preferred solvent in the process is EtOH.

Concentrations of I in the solvent can range from 0.001 to 1 molar and preferably 0.1 to 1 molar.

Temperature employed in the hydrogenation process can range from −78° C. up to the boiling point of the solvent. The preferred temperature range for conducting the process is about 0° to 25° C.

Pressure employed in the process can be anywhere from one atmosphere to several atmospheres suitable for standard olefin reduction conditions. Preferred is a pressure of about 0-40 psig and particularly about 40 psig, containing a substantially hydrogen atmosphere. The hydrogen atmosphere can of course contain other gases which are either reducing or inert under the reaction conditions such as small amounts of carbon monoxide or carbon dioxide and the like. Preferably the atmosphere used in the hydrogenation is substantially a hydrogen atmosphere.

The time involved in the hydrogenation is that sufficient under the reaction conditions to obtain substantial catalytic hydrogenation of structural formula I to obtain a resulting β/α epimer molar ratio of greater than 1. β/α epimer molar ratios of substantially greater than 1 are achieved, being generally 1.5 and above and can approach a ratio of 9:1 via the hydrogenation step.

The compounds encompassed by structural Formula I include those compounds wherein $R^2$ is independently selected from H, linear or branched $C_1$-$C_3$ alkyl, which can be substituted with fluoro, hydroxy or protected hydroxy. The hydroxy protecting groups included herein are known in the antibiotic art, are removable by acid or base hydrolysis, and include, inter alia, trialkylsilicon groups such as t-butyldiphenylsilyl, triphenylsilyl, isopropyldimethylsilyl or dimethyl-t-butylsilyl.

A preferred hydroxy protecting silyl group, e.g. t-butyldimethylsilyloxy can be formed by reacting the hydroxy group, e.g. 1-hydroxyethyl, with t-butyldimethylsilyl chloride in a dry solvent such as methylene chloride, DMF, or other inert solvents, in the presence of an acid acceptor, e.g. triethylamine or imidazole, at −20° to 25° C. for a period of 1-2 hours and then isolating and purifying the desired protected hydroxy compound by conventional methods.

When desired to remove the protecting group, such as prior to hydrogenation, the protected silyloxy can be treated with fluoride, e.g. with tetrabutylammonium fluoride in tetrahydrofuran in dimethylformamide solvent at room temperature for 1-2 hours. Isolation and purification of the resulting hydroxy compound can be accomplished by conventional procedures. Generally, in the hydrogenation step of the methylene double bond, it is preferred to deblock the hydroxy group when present in $R^2$ prior to the hydrogenation.

Representative examples of $R^2$ include H, $CH_3-$, $CH_3CH_2-$, $(CH_3)_2CH-$, $HOCH_2-$, $CH_3CHOH-$, $CH_3CH[OSi[C(CH_3)_3](CH_3)_2]-$, $(CH_3)_2COH-$, $FCH_2-$, $F_2CH-$, $F_3C-$, $CH_3CHF-$, $CH_3CF_2-$, $(CH_3)_2CF-$, $CH_3CH_2CHOH-$ and $FCH_2CHOH-$. Preferred is where $R^2$ is $CH_3CHOH-$.

Y is a bridging-protecting group derived from an aldehyde, ketone or organosilicon compound, or equivalent thereof, including acetals, ketals, and the like and includes $(CH_3)_2C<$,

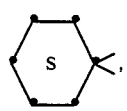

$(t\text{-Bu})_2\text{Si}<$,

and substituted derivatives thereof, wherein said substituents are inert during the subject process described herein and include, inter alia, $C_1$–$C_4$ lower alkyl and alkoxy.

Representative examples of aldehydes, ketones and organosilicon compounds which are precursors for Y include those which are known in the antibiotic art, e.g., acetone, 2,2-dimethoxypropane, cyclohexanone, 1,1-dimethoxycyclohexane, methylethylketone, 2,2-diethoxy-n-butane, acetaldehyde, acetaldehyde dimethylacetal, acetophenone, p-methoxyacetophenone, dichlorodimethylsilane, dichlorodiphenylsilane, dichloroethylphenylsilane, dichlorodi-t-butylsilane and the like. A preferred reagent for forming the Y moiety is 2,2-dimethoxypropane wherein the Y moiety is formed by reacting the deblocked amino alcohol of structure V for example with 2,2-dimethoxypropane in the presence of a catalyst such as boron trifluoride etherate, toluenesulfonic acid, or the like in a solvent such as methylene chloride, ether, chloroform, dioxane or the like at a temperature of from $-10°$ C. to $35°$ C. for from a few minutes to 1 hour.

The bridging-protecting group Y, not readily removable by hydrogenation, is removable by acid or base hydrolysis as described in the reference U.S. Pat. No. 4,234,596, hereby incorporated by reference for that purpose.

Structure I is derived as described above from the reaction of ketone, aldehyde or organosilicon compound with the deblocked amino-alcohol V, where $R^3$ and $R^6$ are H:

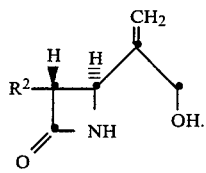

Representative examples of structure I include:

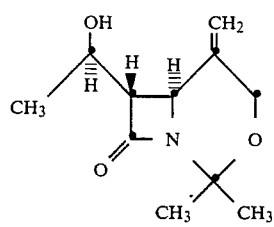

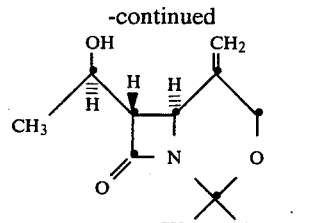

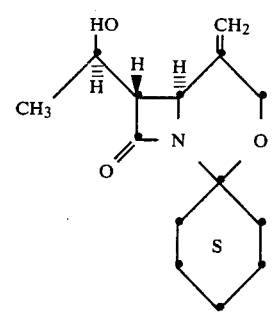

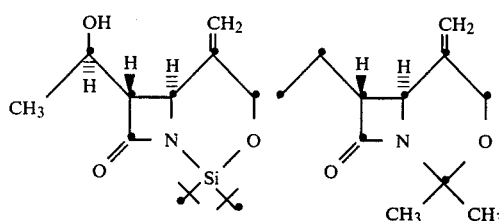

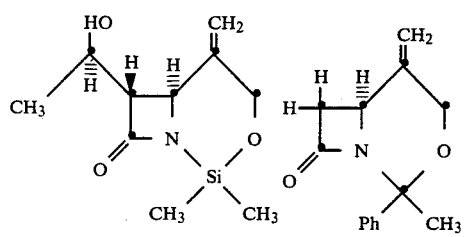

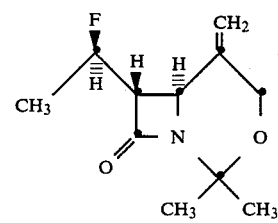

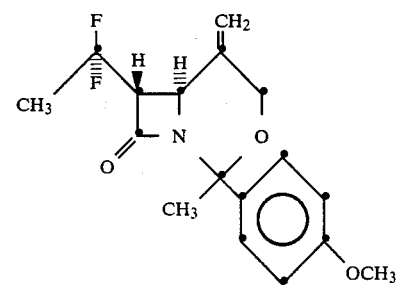

Further examples of Structure I for illustration purposes are given below in the Table indicating specific values chosen for $R^2$ and bridging-protecting group Y.

TABLE

| Compound | R² | Y |
|---|---|---|
| 1 | H | (t-Bu)₂Si= |
| 2 | H | Ph₂SI= |
| 3 | H | (thiophene)= |
| 4 | H | (CH₃)₂C= |
| 5 | CH₃ | (CH₃)₂C= |
| 6 | CH₃ | (thiophene)= |
| 7 | CH₃ | (CH)₃Si= |
| 8 | CH₃ | Ph(CH₃CH₂)Si= |
| 9 | CH₃CH₂CH₂ | Ph(CH₃CH₂)Si= |
| 10 | CH₃CH₂CH₂ | Ph₂Si= |
| 11 | CH₃CH₂CH₂ | CH₃CH₂C(CH₃)= |
| 12 | CH₃CH₂CH₂ | C₆H₄-C(CH₃)= |
| 13 | (CH₃)₂CH | (CH₃)₂C= |
| 14 | (CH₃)₂CH | (thiophene)= |
| 15 | (CH₃)₂CH | (t-Bu)₂Si= |
| 16 | (CH₃)₂CH | Ph₂Si= |
| 17 | HOCH₂ | Ph₂Si= |
| 18 | HOCH₂ | (CH₃)(CH₃CH₂)Si= |
| 19 | HOCH₂ | MeO-C₆H₄-C(CH₃)= |
| 20 | HOCH₂ | (CH₃)₂C= |
| 21 | (CH₃)₂COH— | (CH₃)₂C= |
| 22 | (CH₃)₂COH— | CH₃CH₂—C(CH₃)= |
| 23 | (CH₃)₂COH— | (CH₃)₂Si= |
| 24 | (CH₃)₂COH— | Ph₂Si= |
| 25 | FCH₂— | Ph₂Si= |
| 26 | FCH₂— | (t-Bu)₂Si= |
| 27 | FCH₂— | C₆H₄-C(CH₃)= |
| 28 | FCH₂— | (thiophene)= |
| 29 | F₂CH | (thiophene)= |
| 30 | F₂CH | (CH₃)₂C= |
| 31 | F₂CH | Ph₂Si= |
| 32 | F₂CH | (t-Bu)₂Si= |
| 33 | F₃C | (t-Bu)₂Si= |
| 34 | F₃C | (CH₃)₂Si= |
| 35 | F₃C | C₆H₄-C(CH₃)= |
| 36 | F₃C | MeO-C₆H₄-C(CH₃)= |
| 37 | (CH₃)₂CF | MeO-C₆H₄-C(CH₃)= |
| 38 | (CH₃)₂CF | (CH₃)₂C= |
| 39 | (CH₃)₂CF | Ph₂Si= |
| 40 | (CH₃)₂CF | (CH₃)₂Si= |

The structures and formulae representative of Structure I given in the above Table are not meant to be limiting and other combinations of R² and Y and their resulting species of Structure I which will be obvious to one skilled in the art from this disclosure are also deemed to be included within the scope of the invention.

A preferred compound of structure I for use in the process is:

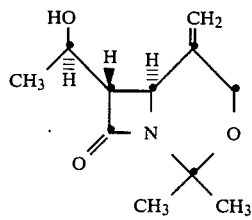

A synthesis of a species of general structure I is given below in the Flow Sheet for converting the monocyclic β-lactam ring system into the bicyclic system, 8-oxo-3-oxa-1-azabicyclo[4.2.0]octane with the exocyclic methylene group alpha to the beta lactam ring and a 1-hydroxyethyl radical adjacent to the beta lactam carbonyl.

By the same general procedure, the compounds encompassed by Structure I, where R² and Y have other values disclosed herein, within the claimed definition, are also obtained.

FLOW SHEET

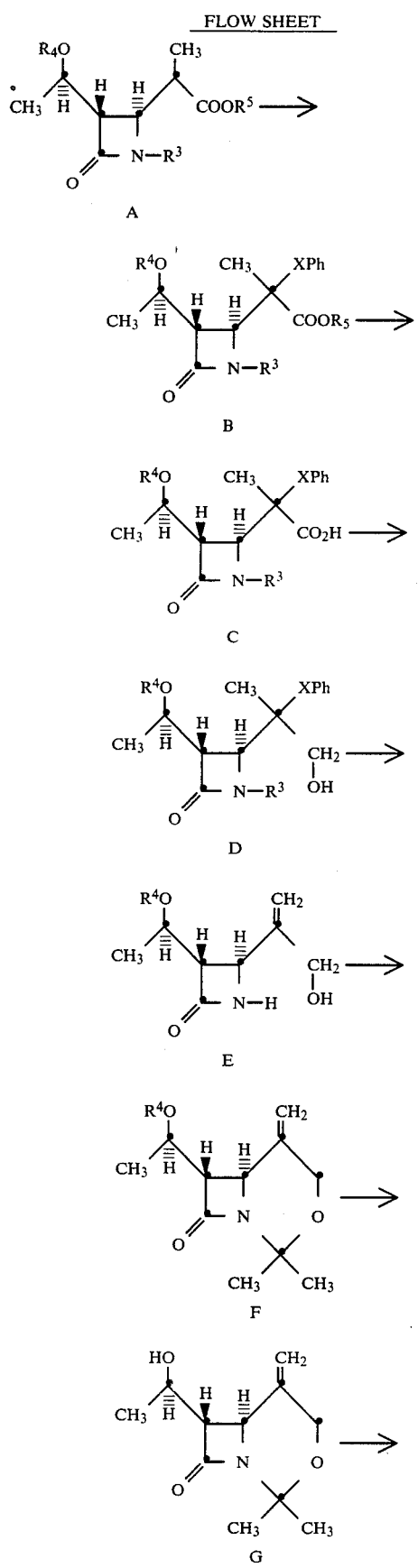

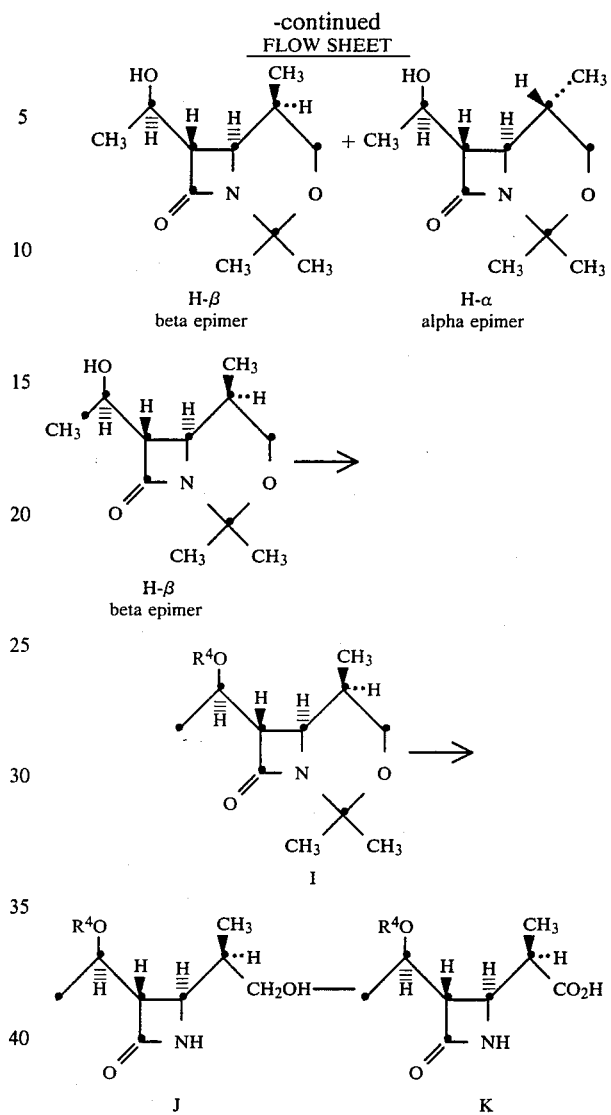

In words relative to the above Flow Sheet, starting compound A with the indicated stereochemistry where $R^4$ is H or t-butyldimethylsilyl, is known and can be synthesized by the method described in the above-cited *Heterocycles* reference, hereby incorporated by reference for this particular purpose.

The selenation or sulfenylation of A to B is conducted under dry and $O_2$-free conditions, preferably under nitrogen, by treating A with a proton-abstracting agent such as LDA (lithium diisopropylamide) in an anhydrous solvent such as THF (tetrahydrofuran), and in the presence of HMPA (hexamethylphosphoramide) to increase rate of reaction, followed by treating with a selenation or sulfenylation agent. Other proton abstracting agents which can be used are lithium hexamethyldisilazide, NaH, lithium cyclohexylisopropylamide, and the like. Preferred is LDA. Other solvents which can be used in this particular step are glyme, diethylether, dimethylformamide, and the like. The solvent should be dry and inert under the reaction conditions and preferred is tetrahydrofuran.

The selenating agent used is a diselenide (or a disulfide if sulfenylating such as diphenyldisulfide), preferably diphenyldiselenide, and the reaction is carried out at −78° C. to 0° C. under nitrogen atmosphere for a period of time of about 1 to 8 hours to achieve a desired yield of the selenated compound B. The same procedure for sulfenylating can be generally used with the corresponding disulfide. A mixture of alpha and beta selenides is produced, but it is not absolutely necessary to perform a separation step since either diastereomer or a mixture can be used in the later oxidation step to produce the methylene compound.

The resulting selenated ester B is hydrolyzed to the acid C by conventional alkaline hydrolysis in e.g., aqueous methanol at a temperature of about 25° to 60° C., for about 2 to 24 hours, under a nitrogen atmosphere, to obtain desirable yields of compound C. Other solvent combinations can also be used, e.g. aqueous ethanol.

The resulting acid C is reduced to the primary alcohol D by a suitable reducing agent, including $BH_3.Me_2S$ in solvent THF, at a temperature of 0° to 65° C., for about 2 to 24 hours under a nitrogen atmosphere to achieve the alcohol. Other reducing agents such as lithium aluminum hydride and borane can also be used which are not detrimental to the beta-lactam ring.

The alcohol selenide D is then treated with an oxidizing agent such as hydrogen peroxide in acetic acid/THF solvent to form E having the exocyclic double bond at the α-position to the B-lactam ring. Generally this step is conducted at about 0° to 100° C., for a period of time of about 1 to 24 hours. Other oxidizing agents which can be used include m-chloroperbenzoic acid, ozone, and $NaIO_4$ in solvents including methylene chloride, toluene, and EtOH. Preferred oxidizing system is hydrogen peroxide in acetic acid/THF solvent.

Following the above oxidation-elimination procedure, the ring nitrogen is deblocked, if a conventional blocking group is present, by the procedure of acid or base catalyzed hydrolysis, but not hydrogenation, and the amino alcohol is joined together by reaction with a divalent bridging-protecting group as described herein such as 2,2-dimethoxypropane, or the like, in a suitable solvent and presence of a Lewis acid such as $BF_3.Et_2O$, p-toluenesulfonic acid, chlorosulfonic acid to form F. Other bridging-protecting agents which can also be used are cyclohexanone, p-methoxyacetophenone or its dimethylketal, or a diorganodichlorosilane such as di-t-butyldichlorosilane. Preferred is 2,2-dimethoxypropane, reacted in methylene chloride solvent. Following cyclization the 1'-hydroxy group is deblocked by treating with tetrabutylammonium fluoride in DMF to form G. The deblocking of the 1'-hydroxy group has been found to be highly favorable in obtaining a high ratio of β/α epimers in the subsequent reduction step.

Following the deblocking step to yield G, the reduction is carried out as described hereinabove with Raney Nickel, to yield a mixture of the β-methyl and α-methyl epimers H, being H-β and H-α, respectively, with the β-methyl epimer predominating. The resulting β- and α-isomers can be separated by high pressure liquid chromatography (HPLC), as for example, on a Pre PAK 500/silica column as in conventional practice or by fractional crystallization or the like to obtain the β-epimer in high purity.

The β-epimer once obtained in high purity, can be converted to I and then J by using the methods described in U.S. Pat. No. 4,234,596 hereby incorporated by reference for that purpose.

The reaction H-β→I establishes the blocking group $R^4$ and is typically accomplished by treating H-β with a base such as an alkali metal hydroxide, lithium diisopropyl amide, 4-dimethylaminopyridine, or n-butyllithium in a solvent such as methylene chloride, ether, THF, dioxane, DMF, DMSO or the like, followed by treatment with an acyl halide of choice such as an alkanoyl, aralkanoyl or nuclear substituted aralkanoyl, or alkyl, aryl or aralkyl, substituted aralkyl or substituted aryl haloformate such as allylchloroformate or p-nitrobenzylchloroformate or the like at a temperature of from −78° C. to 25° C. for from 1-24 hours.

Alternatively, the protecting group $R^4$ may be a triorganosilyl group, such as t-butyldimethylsilyl, t-butyldiphenylsilyl, triphenylsilyl, isopropyldimethylsilyl, for example, or may be 3,4-dimethoxybenzyl, for example. Typically $R^4$ is established by treating H-β in a solvent such as $CH_2Cl_2$, dimethylformamide, acetonitrile, hexamethylphosphoramide, tetrahydrofuran and the like with a silylating agent such as t-butyldimethylchlorosilane, t-butyldiphenylchlorosilane, triphenylchlorosilane, and the like at a temperature of from −20° to 25° C. for from 0.5 to 24 hours in the presence of a base such as triethylamine, diisopropylethylamine, or imidazole or 4-dimethylaminopyridine.

The de-blocking reaction I→J is typically conducted by acid hydrolysis such as aqueous acetic acid at a temperature of from 25° C. to 75° C. for from 5 minutes to 3 hours.

The oxidation of J to K is accomplished by treating J in a solvent such as acetone or the like with Jones reagent at from −78° to 25° C. for from one minute to 2 hours. Alternatively, the conversions I to J to K may be done in one step by treatment of I as above with Jones reagent to give K directly.

The carboxylic acid K can then be be treated for example, by the method described in the above-cited *Heterocycles* reference and U.S. Pat. Nos. 4,383,946 and 4,309,346, all hereby incorporated by reference for this purpose, to arrive at subsequent active 1-β-methylcarbapenem antibiotics, including (−)-(1R,5S,6S)-2-(2-N,N-dimethylamino-2-iminoethylthio)-6-[(1R)-1-hydroxyethyl]-1-methylcarbapen-2-em-3-carboxylic acid, useful as described hereinabove.

Preferred process for selectively reducing an exocyclic α-methylene ring double bond of the invention comprises the step of contacting the compound:

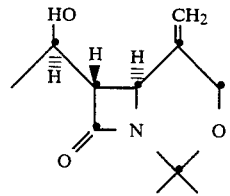

in an organic solvent therefor as described hereinabove, with a hydrogen atmosphere at about 40 psig reaction pressure with Raney nickel catalyst for a time sufficient to obtain a mixture of α-methyl and β-methyl epimers in a β to α epimeric molar ratio of greater than 1.

Methods of synthesis are given below in the Diagram, Schemes, and discussion, for other starting compounds A, where radical $R_2$ on the beta lactam ring is chosen from other groups within the claimed definition therefor. The methods are taken from U.S. Pat. No. 4,309,346 and U.S. Pat. No. 4,383,946, which are incorporated by reference specifically for this purpose.

DIAGRAM I

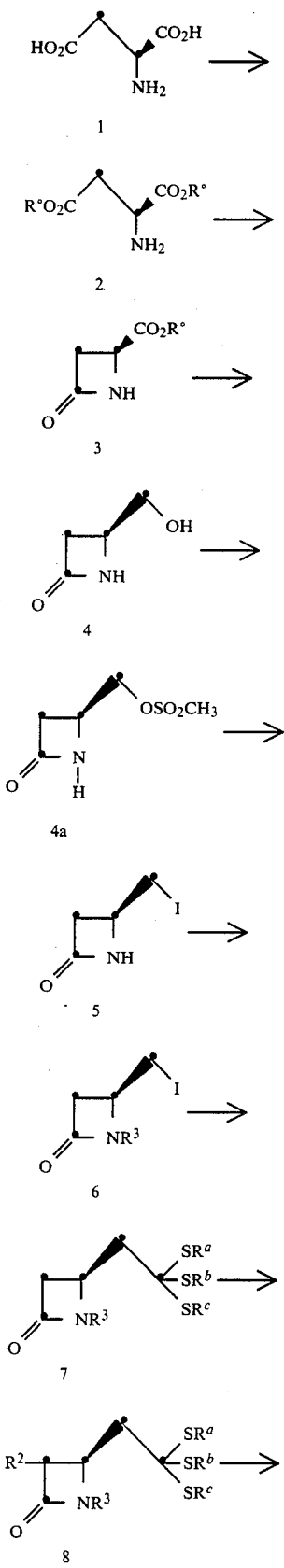

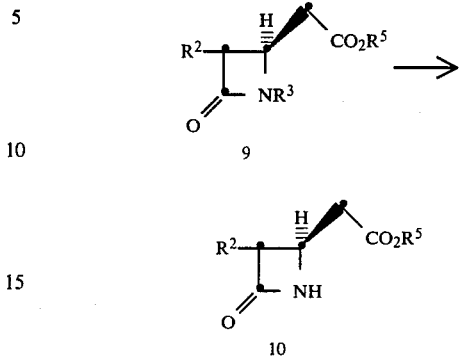

-continued
DIAGRAM I

In words relative to the above diagram, L-aspartic acid 1 is esterified according to well known procedures. R° is a protecting group such as benzyl, methyl, ethyl, isopropyl or the like. Typically 1 in a solvent such as benzene, toluene, chloroform or the like is treated with an esterifying agent such as benzyl alcohol, methanol, ethanol, isopropanol, or the like in the presence of p-toluene sulfonic acid, HCl, HBr, or the like at a temperature of from 0° to 100° C. for from 1 to 24 hours to achieve the desired establishment and hence protection of the carboxyl functions. The resulting species 2 in a solvent such as ether, THF, DME or the like is treated with trimethylchlorosilane, or the like followed by treatment with EtMgBr, MeMgI, ∅MgBr, t-BuMgCl, or the like at a temperature of from $-40°$ to $50°$ C. for from 1 to 72 hours to provide azetidinone 3. Reduction of species 3 with a reducing agent such as $NaBH_4$, or the like in a solvent such as methanol, ethanol, isopropanol or the like at a temperature of from $-10°$ to $40°$ C. for from 1 to 6 hours provides 4. (For purposes here, the symbols: Et, Me, ∅, iPr, and t-Bu stand for: ethyl, methyl, phenyl, isopropyl, and tert-butyl, respectively.)

Treatment of 4 in a solvent such as methylene chloride, $CHCl_3$ or the like with methane sulfonyl chloride, methane sulfonic anhydride or the like in the presence of a base such as $Et_3N$, $iPr_2NEt$, or the like followed by treatment with a stoichiometric to 5-fold excess of sodium iodide in acetone yields 5 via 4a.

The transformation 5→6 establishes the protecting group $R^3$ which may be a triorganosilyl group, such as t-butyldimethylsilyl, t-butyldiphenylsilyl, triphenylsilyl, isopropyldimethylsilyl, for example, or may be 3,4-dimethoxybenzyl, for example. Silyl protection is preferred, and typically $R^3$ is established by treating 5 in a solvent such as dimethylformamide, acetonitrile, hexamethylphosphoramide, tetrahydrofuran and the like with a silylating agent such as t-butyldimethylchlorosilane, t-butyldiphenylchlorosilane, triphenylchlorosilane, and the like at a temperature of from $-20°$ to $25°$ C. for from 0.5 to 24 hours in the presence of a base such as triethylamine, diisopropylethylamine, or imidazole.

The transformation 6→7 is accomplished by treating 6 in a solvent such as tetrahydrofuran, dimethoxyethane, diethylether or the like with a carbanion generically represented by the following structure:

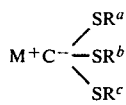

wherein M is a metal cation such as lithium, potassium, copper or magnesium, for example, and $R^a$, $R^b$ and $R^c$ are selected from alkyl, aryl or aralkyl such as methyl, ethyl, benzyl, methoxybenzyl, trityl and phenyl, for example, at a temperature of from −100° to 0° C. and from 0.5 to 4 hours.

Typically, the carbanion reagent is prepared prior to addition of substrate 6 on treatment of the triorganothiomethane with a strong base such as n-butyllithium, t-butyllithium, phenyllithium, lithium diisopropylamide (LDA) or the like.

Resulting intermediate 7 can be mono-, or dialkylated at ring position 3. Alkylation of 7 provides 8. Typically, 7 is treated with a strong base such as lithium diisopropylamide, lithium 2,2,6,6-tetramethylpiperidide, potassium hydride, lithium hexamethyldisilazide, phenyllithium or the like in a solvent such as tetrahydrofuran (THF), hexamethylphosphoramide, ether, dimethoxyethane, and the like at a temperature of from −80° C. to 0° C. whereupon the alkylating agent of choice, $R^2X°$ is added (X° is chloro, iodo or bromo); alternatively the alkylating agent may be $R^2$-tosylate, $R^2$-mesylate or an aldehyde or ketone such as acetaldehyde to provide monoalkylated species 8.

The eventual 6-substituents (nomenclature relative to final, bicyclic structure) can also be established by direct acylation using an acylating agent such as N-acyl imidazole or the like. Such N-acyl imidazole acylating reagents are listed below. Also given below is a detailed description of this second approach for establishing $R^2$.

The following list is representative of useful alkylating agents for establishing $R^2$, according to the above scheme: 7→8 (this will be referred to as Scheme I, to be distinguished from Scheme II, below, which involves acylation):

| Alkylating Agents |
|---|
| CH₃CHO |
| CH₂O |
| CH₃I |
| CH₃COCH₃ |
| CH₃CH₂Br |
| (CH₃)₂CHBr |
| CH₃CH₂CHO |
| CF₃CHO |
| CHF₂CHO |
| CH₂FCHO |
| F₂CHI |
| F₃CI |
| CH₃CF₂I |

The fluoro compounds CH₃CHF—, and F—CH₂—, can be prepared from the corresponding hydroxy compounds by treating the hydroxy compound with DAST ™, diethylaminosulfur trifluoride, in an inert solvent such as THF, at a temperature of −78° to 25° C. under an inert atmosphere for a period of about 1 to 2 hours. As mentioned above, the 6-substituents may also be established by acylation. Utilization of such acylating agents may be demonstrated in the following manner with regard to a preferred starting, or intermediate, material 8.

SCHEME II

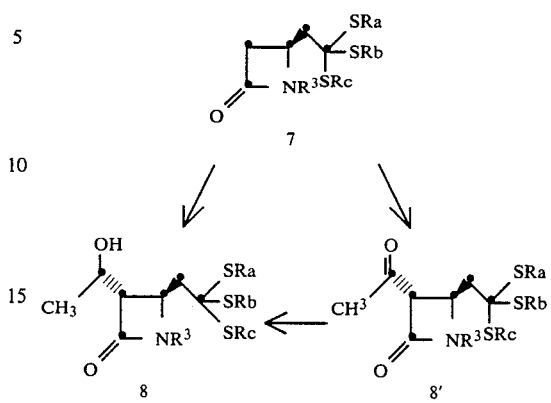

The alkylation 7→8, is accomplished as previously described, by treating 7 in a solvent such as tetrahydrofuran, dimethoxyethane, diethylether, hexamethylphosphoramide, at a temperature of from −100° to −20° C. with a strong base such as lithium diisopropylamide, lithium hexamethyldisilazide, lithium 2,2,6,6-tetramethylpiperidide, potassium hydride or the like followed by the addition of an equivalent to 10 fold excess of an aldehyde. This reaction gives a mixture of isomers from which the desired trans-R form 8 can be conveniently separated by known methods of chromatography or crystallization. Intermediate 7 may proceed directly to 8 as indicated above, Scheme I, or it may take the circuitous path via 8'. The direct acylation, to 8' is accomplished by treating 7 with two or more equivalents of a base such as lithium diisopropylamide, lithium hexamethyldisilazide, lithium 2,2,6,6-tetramethylpiperidide, in a solvent such as tetrahydrofuran, diethylether, or dimethoxyethane, for example, at a temperature of from −100° to −20° C. with an acylating agent such as N-acyl imidazole or the like. Addition of the 7 plus base mixture to the acylating agent is preferred.

Representative acylating agents for this scheme 7→8'→8 are listed below.

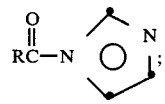

R=CH₃, CH₃CH₂, CH₃OCH₂, CF₃, CF₂H, CH₂F.

Further with respect to Scheme II, the reduction 8'→8 is accomplished by contacting the ketone with a reducing agent such as potassium tri(sec-butyl)borohydride, lithium tri(sec-butyl)borohydride, sodium borohydride, sodium tris(methoxyethoxy)aluminum hydride, lithium aluminum hydride or the like in a solvent such as diethylether, tetrahydrofuran, toluene or the like at a temperature of from −78° to 25° C. The reaction can conveniently be conducted in the presence of an added complexing salt such as potassium iodide, magnesium bromide or the like.

In a similar manner, unresolved 8 (cis and trans) may be oxidized to 8' for reduction to 8 as indicated above:

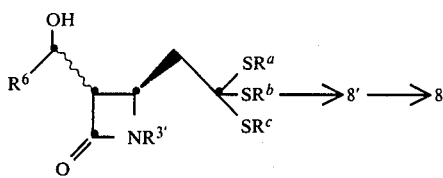

The oxidation is accomplished with an oxidizing agent such as dipyridine chromium (VI) oxide, trifluoroacetic anhydride-dimethylsulfoxide-triethylamine, pyridinium dichromate, acetic anhydride-dimethylsulfoxide in a solvent such as methylene chloride, acetonitrile, or the like at a temperature of from −78° to 25° C. for from 5 minutes to 5 hours.

Now return to the main scheme of synthesis, Diagram I, and the transformation 8→9, which is accomplished by treating 8 in a solvent such as methanol, ethanol, isopropanol, water or the like at a temperature of from 0° to 80° C. with a Lewis acid such as mercuric chloride, silver tetrafluoroborate, thallium trinitrate or the like. The value of $R^5$ is determined by the identity of the alcohol taken in reaction.

The triorganylsilyl protecting group $R^3$ may then be removed from 9 to give 10 by treatment with fluoride, e.g. tetrabutylammonium fluoride in tetrahydrofuran, in a solvent such as tetrahydrofuran, dimethylformamide, ether or the like at a temperature of from −78° to 25° C. for from 1 minute to 2 hours.

The mono-alkylated products 8 through 10, in which $R^2$ does not contain a chiral center, will exist as a mixture of cis and trans structures:

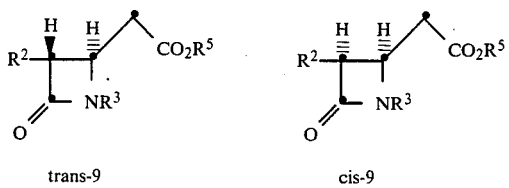

the configurational isomerism referring to the 3- and 4-hydrogen atoms on the ring. The desired isomer, trans-8 through 10, can be obtained by known methods in the art including crystallization and chromatography. The resulting trans-10 form can be used directly in producing the desired 1-betamethyl intermediates, by following the procedure in Heterocycles, supra, wherein trans-10 is treated with two equivalents of lithium diisopropylamide (LDA) in THF containing one equivalent of HMPA (hexamethylphorphoramide) at −78° C. followed by excess methyl iodide yields a mixture of the alpha and beta methyl isomers which is then selenated and carried through the remaining steps as indicated in the Flow Sheet.

An alternate route for producing the intermediates:

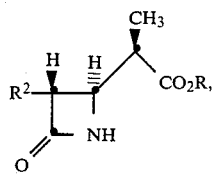

where $R^2=CH_3CHOH—$, is given in U.S. Pat. No. 4,206,219, hereby incorporated by reference for this particular purpose.

Also a subject of the instant invention are the compositions produced in the above-described process of forming the exocyclic double bond leading to the desired 1-β-methylcarbapenem intermediates being compositions of the Formula:

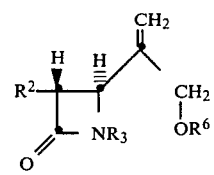

wherein $R^2$ is independently selected from hydrogen, linear or branched $C_1-C_3$ alkyl, which can be substituted with fluoro, hydroxy or protected hydroxy, $R^3$ is hydrogen or a protecting group, $R^6$ is hydrogen, a protecting group, or a covalent bond, and where $R^6$ is a covalent bond, $R^3$ and $R^6$ are joined to form Y, a divalent bridging-protecting group, derived from a ketone, aldehyde or organosilicon compound, said group being stable to catalytic hydrogenation and removable by acid or base hydrolysis. The protecting groups $R^3$ and $R^6$ are also removable by acid or base hydrolysis and include the triorganosilyl groups known in the art as also represented by $R^4$ in Structure A.

The compositions include these wherein said $R^2$ is independently selected from H, $CH_3—$, $CH_3CH_2—$, $(CH_3)_2CH—$, $HOCH_2—$, $CH_3CHOH—$, $(CH_3)_2COH—$, $FCH_2—$, $F_2CH—$, $F_3C—$, $CH_3CHF—$, $CH_3CF_2$, $(CH_3)_2CF—$, $CH_3CH_2CHOH—$, $FCH_2CHOH—$, and wherein said Y includes $(CH_3)_2C<$,

$(t-Bu)_2Si<$, or

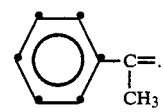

Representative Examples of Structure V which include Y through the coupling of $R^3$ and $R^6$ resulting in Structure I are adequately illustrated hereinabove and need not be reiterated but are incorporated by reference herein as supplementing disclosure.

Representative Examples of Structure V where $R^3$ and $R^6$ have other values than Y are presented in the following Table:

TABLE

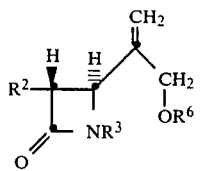

V

| Compound | R² | R³ | R⁶ |
|---|---|---|---|
| 1 | H | H | H |
| 2 | CH₃ | H | H |
| 3 | CH₃CH₂ | H | H |
| 4 | CH₃CH₂CH₂ | H | H |
| 5 | (CH₃)₂CH | H | H |
| 6 | HOCH₂ | H | H |
| 7 | CH₃CHOH | H | H |
| 8 | (CH₃)₂COH | H | H |
| 9 | DMTBS—OCH₂ | H | H |
| 10 | DPTBS—OCH₂ | H | H |
| 11 | TPS—OCH₂ | H | H |
| 12 | IPDMS—OCH₂ | H | H |
| 13 | CH₃CH(O—DMTBS)— | H | H |
| 14 | CH₃CH(O—DPTBS)— | H | H |
| 15 | CH₃CH(O—TPS) | H | H |
| 16 | CH₃CH(O—IPDMS) | H | H |
| 17 | (CH₃)₂C(O—DMTBS) | H | H |
| 18 | (CH₃)₂C(O—DPTBS) | H | H |
| 19 | (CH₃)₂C(O—TPS) | H | H |
| 20 | (CH₃)₂C(O—IPDMS) | H | H |
| 21 | FCH₂ | H | H |
| 22 | F₂CH— | H | H |
| 23 | F₃C— | H | H |
| 24 | CH₃CHF | H | H |
| 25 | CH₃CF₂ | H | H |
| 26 | (CH₃)₂CF— | H | H |
| 27 | H | IPDMS | H |
| 28 | CH₃ | IPDMS | H |
| 29 | CH₃CH₂ | IPDMS | H |
| 30 | CH₃CH₂CH₂ | IPDMS | H |
| 31 | (CH₃)₂CH | DMTBS | H |
| 32 | HOCH₂ | DMTBS | H |
| 33 | CH₃CHOH | DMTBS | H |
| 34 | (CH₃)₂COH | DMTBS | H |
| 35 | DMTBS—OCH₂ | DPTBS | DPTBS |
| 36 | DPTBS—OCH₂ | DPTBS | DPTBS |
| 37 | TPS—OCH₂ | DPTBS | DPTBS |
| 38 | IPDMS—OCH₂ | DPTBS | DPTBS |
| 39 | CH₃CH(O—DMTBS) | TPS | H |
| 40 | CH₃CH(O—DPTBS) | TPS | IPDMS |
| 41 | CH₃CH(O—TPS) | TPS | DMTBS |
| 42 | CH₃CH(O—IPDMS) | TPS | DPTBS |
| 43 | (CH₃)₂C(O—DMTBS) | H | IPDMS |
| 44 | (CH₃)₂C(O—DPTBS) | H | DMTBS |
| 45 | (CH₃)₂C(O—TPS) | H | DPTBS |
| 46 | (CH₃)₂C(O—IPDMS) | H | TPS |
| 47 | FCH₂ | IPDMS | H |
| 48 | F₂CH | IPDMS | H |
| 49 | F₃C | IPDMS | H |
| 50 | CH₃CHF | DMTBS | H |
| 51 | CH₃CF₂ | DMTBS | H |
| 52 | (CH₃)₂CF | DMTBS | H |

The abbreviations used:
IPDMS = isopropyldimethylsilyl
DMTBS = dimethyl-t-butylsilyl
DPTBS = diphenyl-t-butylsilyl
TPS = triphenylsilyl The structures and formulas representative of Structure V given in the above Table are not meant to be limiting, and other combinations of R², R³ and R⁶ and their resulting species of Structure V, which will be obvious to one skilled in the art in light of this disclosure are also deemed to be included within the scope of this invention.

Preferred compositions of Structure V are:

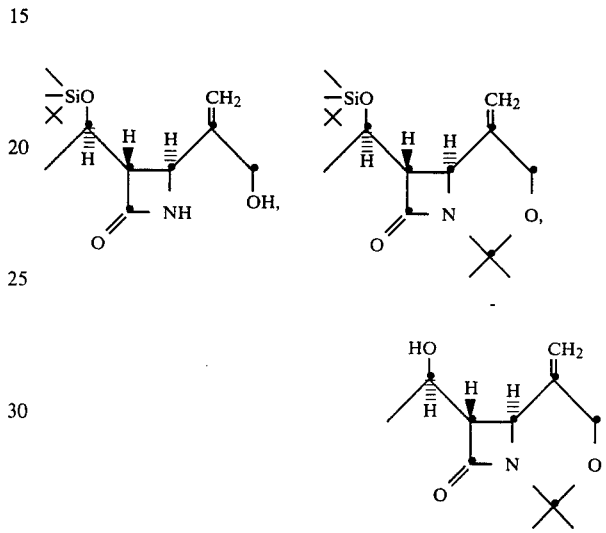

Also a subject of the invention are the intermediate compositions to I of the Structural formula:

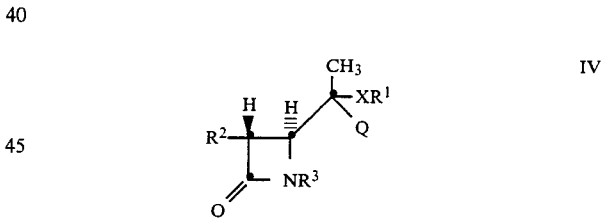

IV wherein R² is described hereinabove; R³ is hydrogen or a blocking group, X is sulfur or selenium, Q is hydroxymethyl, carboxy or $C_1$-$C_4$ alkoxycarbonyl, and R¹ is $C_1$-$C_4$ alkyl, $C_6$-$C_{10}$ aryl, heteroaryl, said aryl and heteroaryl can contain substituents including $C_1$-$C_4$ alkyl and alkoxy, nitro and the like, which are inert under the reaction conditions. By the term "substituted phenyl" is meant substituents inert under the reaction conditions leading to the synthesis of structure I and include $C_1$-$C_4$ alkyl, alkoxy, nitro and the like.

Representative Examples of Structure IV are given in the following Table.

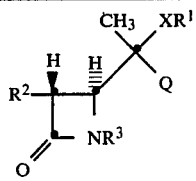

IV

| Compound | R¹ | R² | R³ | Q | X |
|---|---|---|---|---|---|
| 1 | Ph | H | H | HOCH$_2$ | Se |
| 2 | Ph | CH$_3$ | H | HOCH$_2$ | Se |
| 3 | Ph | CH$_3$CH$_2$ | H | HOCH$_2$ | Se |
| 4 | Ph | CH$_3$CH$_2$CH$_2$ | H | HOCH$_2$ | Se |
| 5 | Ph | (CH$_3$)$_2$CH | H | HOCH$_2$ | Se |
| 6 | Ph | HOCH$_2$ | H | HOCH$_2$ | Se |
| 7 | Ph | CH$_3$CHOH | H | HOCH$_2$ | Se |
| 8 | Ph | (CH$_3$)$_2$COH | H | HOCH$_2$ | Se |
| 9 | Ph | F—CH$_2$ | H | HOCH$_2$ | Se |
| 10 | Ph | F$_2$CH | H | HOCH$_2$ | Se |
| 11 | Ph | F$_3$C | H | HOCH$_2$ | Se |
| 12 | Ph | CH$_3$CHF | H | HOCH$_2$ | Se |
| 13 | Ph | CH$_3$CF$_2$ | H | HOCH$_2$ | Se |
| 14 | Ph | (CH$_3$)$_2$CF | H | HOCH$_2$ | Se |
| 15 | Ph | DMTBS—OCH$_2$ | H | HOCH$_2$ | Se |
| 16 | Ph | DPTBS—OCH$_2$ | H | HOCH$_2$ | Se |
| 17 | Ph | TPS—OCH$_2$ | H | HOCH$_2$ | Se |
| 18 | Ph | IPDMS—OCH$_2$ | H | HOCH$_2$ | Se |
| 19 | Ph | CH$_3$CH(O—DMTBS) | H | HOCH$_2$ | Se |
| 20 | Ph | CH$_3$CH(O—DPTBS) | H | HOCH$_2$ | Se |
| 21 | CH$_3$ | CH$_3$CH(O—TPS) | H | HOCH$_2$ | Se |
| 22 | CH$_3$ | CH$_3$CH(O—IPDMS) | H | HOCH$_2$ | Se |
| 23 | CH$_3$ | (CH$_3$)$_2$C(O—DMTBS) | H | HOCH$_2$ | Se |
| 24 | CH$_3$ | (CH$_3$)$_2$C(O—DPTBS) | H | HOCH$_2$ | Se |
| 25 | CH$_3$ | (CH$_3$)$_2$C(O—TPS) | H | HOCH$_2$ | Se |
| 26 | CH$_3$ | (CH$_3$)$_2$C(O—IPDMS) | H | HOCH$_2$ | Se |
| 27 | CH$_3$ | H | H | COOCH$_3$ | Se |
| 28 | CH$_3$ | CH$_3$ | H | COOCH$_3$ | Se |
| 29 | CH$_3$ | CH$_3$CH$_2$ | H | COOCH$_3$ | Se |
| 30 | CH$_3$ | CH$_3$CH$_2$CH$_2$ | H | COOCH$_3$ | Se |
| 31 | CH$_3$ | (CH$_3$)CH | H | COOCH$_3$ | Se |
| 32 | CH$_3$ | HOCH$_2$ | H | COOCH$_3$ | Se |
| 33 | CH$_3$ | CH$_3$CHOH | H | COOCH$_3$ | Se |
| 34 | CH$_3$ | (CH$_3$)$_2$COH | H | COOCH$_3$ | Se |
| 35 | CH$_3$ | FCH$_2$ | H | COOCH$_3$ | Se |
| 36 | CH$_3$ | F$_2$CH | H | COOCH$_3$ | Se |
| 37 | CH$_3$ | F$_3$C | H | COOCH$_3$ | Se |
| 38 | CH$_3$ | CH$_3$CHF | H | COOCH$_3$ | Se |
| 39 | CH$_3$ | CH$_3$CF$_2$ | H | COOCH$_3$ | Se |
| 40 | CH$_3$ | (CH$_3$)$_2$CF | H | COOCH$_3$ | Se |
| 41 | 4-Pyr | DMTBS—OCH$_2$ | H | COOCH$_3$ | Se |
| 42 | 4-Pyr | DPTBS—OCH$_2$ | H | COOCH$_3$ | Se |
| 43 | 4-Pyr | TPS—OCH$_2$ | H | COOCH$_3$ | Se |
| 44 | 4-Pyr | IPDMS—OCH$_2$ | H | COOCH$_3$ | Se |
| 45 | 4-Pyr | CH$_3$CH(O—DMTBS) | H | COOCH$_3$ | Se |
| 46 | 4-Pyr | CH$_3$CH(O—DPTBS) | H | COOCH$_3$ | Se |
| 47 | 4-Pyr | CH$_3$CH(O—TPS) | H | COOCH$_3$ | Se |
| 48 | 4-Pyr | CH$_3$CH(O—IPDMS) | H | COOCH$_3$ | Se |
| 49 | 4-Pyr | (CH$_3$)$_2$C(O—DMTBS) | H | COOCH$_3$ | Se |
| 50 | 4-Pyr | (CH$_3$)$_2$C(O—TPS) | H | COOCH$_3$ | Se |
| 51 | 4-Pyr | (CH$_3$)$_2$C(O—IPDMS) | H | COOCH$_3$ | Se |
| 52 | 4-Pyr | H | DMTBS | COOH | Se |
| 53 | 4-Pyr | CH$_3$ | DMTBS | COOH | Se |
| 54 | p-Tol | CH$_3$CH$_2$ | DMTBS | COOH | Se |
| 55 | p-Tol | CH$_3$CH$_2$CH$_2$ | DPTBS | COOCH$_2$CH$_3$ | Se |
| 56 | p-Tol | (CH$_3$)$_2$CH | DPTBS | COOCH$_2$CH$_3$ | Se |
| 57 | p-Tol | HOCH$_2$ | DPTBS | COOCH$_2$CH$_3$ | Se |
| 58 | p-Tol | CH$_3$CHOH | TPS | COOCH$_2$CH$_2$CH$_3$ | S |
| 59 | p-Tol | (CH$_3$)$_2$COH | TPS | COOCH$_2$CH$_2$CH$_3$ | S |
| 60 | p-Tol | FCH$_2$ | TPS | COOCH$_2$CH$_2$CH$_3$ | S |
| 61 | p-Tol | F$_2$CH | IPDMS | COOCH(CH$_3$)$_2$ | S |
| 62 | p-Tol | F$_3$C | IPDMS | COOCH(CH$_3$)$_2$ | S |
| 63 | p-Tol | CH$_3$CHF | IPDMS | COOCH(CH$_3$)$_2$ | S |
| 64 | p-Tol | CH$_3$CF$_2$ | H | COO(CH$_2$)$_3$CH$_3$ | S |
| 65 | p-Tol | (CH$_3$)$_2$CF | H | COO(CH$_2$)$_3$CH$_3$ | S |
| 66 | p-MeOPh | DMTBS—OCH$_2$ | H | COO(CH$_2$)$_3$CH$_3$ | S |
| 67 | p-MeOPh | DPTBS—OCH$_2$ | H | COOCH$_2$CH(CH$_3$)$_2$ | S |
| 68 | p-MeOPh | TPS—OCH$_2$ | H | COOCH$_2$CH(CH$_3$)$_2$ | S |
| 69 | p-MeOPh | IPDMS—OCH$_2$ | H | COOCH$_2$CH(CH$_3$)$_2$ | S |
| 70 | p-MeOPh | CH$_3$CH(O—DMTBS) | H | COOCH(CH$_3$)CH$_2$CH$_3$ | S |
| 71 | p-MeOPh | CH$_3$CH(O—DPTBS) | H | COOCH(CH$_3$)CH$_2$CH$_3$ | S |
| 72 | p-MeOPh | CH$_3$CH(O—TPS) | H | COOCH(CH$_3$)CH$_2$CH$_3$ | S |

-continued

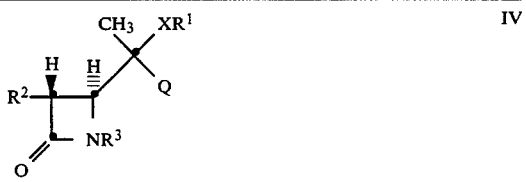

IV

| Compound | R¹ | R² | R³ | Q | X |
|---|---|---|---|---|---|
| 73 | p-MeOPh | CH₃CH(O—IPDMS) | H | COOC(CH₃)₃ | S |
| 74 | p-MeOPh | (CH₃)₂C(O—DMTBS) | H | COOC(CH₃)₃ | S |
| 75 | p-MeOPh | (CH₃)₂C(O—DPTBS) | H | COOC(CH₃)₃ | S |
| 76 | p-MeOPh | (CH₃)₂C(O—TPS) | H | COOC(CH₃)₃ | S |
| 77 | p-MeOPh | (CH₃)₂C(O—IPDMS) | H | COOC(CH₃)₃ | S |

The abbreviations for the silyl protecting groups DMTBS et al. are described hereinabove and for $R^1$ include Ph=phenyl, 4-Pyr=4-pyridyl, p-Tol=p-tolyl and p-MeOPh=p-methoxyphenyl.

The structures and formulas representative of Structure IV given in the above Table are not intended to be limiting, and other combinations of $R^1$, $R^2$, $R^3$, Q and X and their resulting species of Structure IV, which will be obvious to one skilled in the art in light of this disclosure are also deemed to be included within the scope of this invention.

A preferred class of the compositions is of the structural formula:

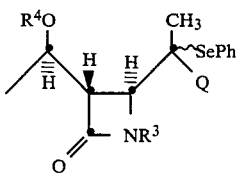

wherein $R^3$ and $R^4$ are independently hydrogen or a blocking group.

Particularly preferred are the compositions of the structural formula:

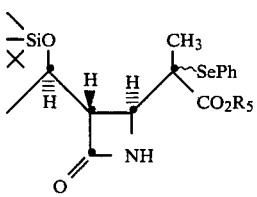

wherein $R^5$ is H or $C_1$-$C_4$ alkyl, preferably methyl.

A further preferred compound is

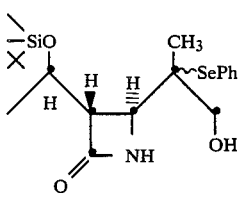

The following examples are illustrative of the best mode of carrying out the invention as contemplated by us and should not be construed to be limitations on the scope or spirit of the instant invention.

EXAMPLE 1

The Stereoselective Preparation of (5R, 6R, 7S)-2,2-Dimethyl-7-[(1'R)-1'-Hydroxyethyl]-5-Methyl-8-Oxo-3-Oxa-1-Azabicyclo[4.2.0]Octane

STEP A

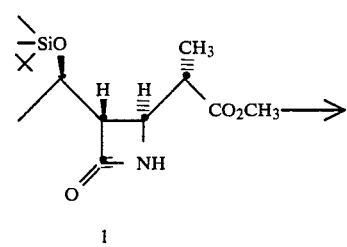

1

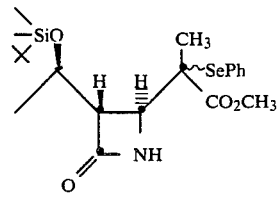

2

At 0° C. under nitrogen, 2.1M n-butyllithium in hexane (9.2 ml, 19.3 mmol) is added to a stirred solution of diisopropylamine (2.68 ml, 19.2 mmol) in anhydrous tetrahydrofuran (40 ml). The temperature is dropped to −78° C. and hexamethylphosphoramide (3.4 ml) is added. After 5 minutes, 1 (2 g, 6.35 mmol) is added in tetrahydrofuran (10 ml), and the reaction mixture is held at −78° C. for 40 minutes. A solution of diphenyldiselenide (3.06 g, 9.81 mmol) in tetrahydrofuran (8 ml) is added. After stirring for 1 hour at −78° C., the reaction mixture is poured into 1M KH₂PO₄ (40 ml) H₂O (400 ml)-Et₂O (200 ml). The organic layer is separated, and the aqueous layer is again extracted with Et₂O (100 ml). The combined ether layers are washed with brine (100 ml), dried over MgSO₄, filtered and concentrated in vacuo to give crude 2 (4.75 g). Chromatography on Baker's silica gel (200 g), gradually eluting with 0% to 50% ethyl acetate in methylene chloride, provides the minor phenylselenyl diastereomer (0.47 g, 16% yield), the major phenylselenyl diastereomer (1.58 g, 53% yield), and recovered starting material (0.35 g, 18% recovery). Efforts were not made to distinguish between the minor and major diastereoisomers as to which was the beta or alpha epimer. The minor diastereomer, or a mixture of diastereomers, can also be treated to give 5, as indicated below for the major isomer, in Steps B-Step D.

The reported nuclear magnetic resonance (NMR) values herein were obtained at 200 or 300 MHz in deuterochloroform solvent, using tetramethylsilane as the internal standard. The values are reported in dimensionless delta ( ) units. Abbreviations used include s=singlet, d=doublet, m=multiplet, br. s.=broad singlet. Coupling constants are reported as J.

Infrared (IR) spectroscopic absorption frequencies taken in methylene chloride solvent are reported for specific functional groups in cm$^{-1}$.

Mass spectrum (ms) data is also presented showing the most abundant mass/charge peak in the spectrum corresponding to the molecular ion (MI) being the molecular weight of the parent, or the trimethylsilyl (TMS) derivative.

Melting points (mp) are presented together with solvent(s) used for recrystallization.

C, H, N Analyses are reported showing *found* and *theoretical* values.

Data for Major Diastereomer 2:

| NMR (CDCl$_3$, TMS): δ |
| --- |
| 0.04 & 0.08 [2 singlets, Si(C$\underline{H}_3$)$_2$] |
| 0.86 [s, SiC(C$\underline{H}_3$)$_3$] |
| 1.31 (d, C$\underline{H}_3$CHOSi) |
| 1.53 (s, C$\underline{H}_3$CSe) |
| 3.06 (m, H$_3$) |
| 3.62 (s, OC$\underline{H}_3$) |
| 4.22 (d, J = 2Hz, H$_4$) |
| 4.26 (m, C$\underline{H}$OSi) |
| 5.80 (br.s., NH) |
| 7.30–7.69 (aromatic protons) |

IR (CH$_2$Cl$_2$) 3400 (NH), 1769 (β-lactam C=O), 1725 (ester C=O) cm$^{-1}$.

mp (recrd. hexane), 115°–118° C.

Anal. calcd. for C$_{21}$H$_{33}$NO$_4$SeSi: C, 53.60; H, 7.07; N, 2.98. Found: C, 53.76; H, 7.28; N, 2.87.

Data for Minor Diastereomer 2:

| NMR (CDCl$_3$, TMS): δ |
| --- |
| 0.07 [s, Si(CH$_3$)$_2$] |
| 0.87 [s, SiC(CH$_3$)$_3$] |
| 1.22 (d, C$\underline{H}_3$CHOSi) |
| 1.48 (s, C$\underline{H}_3$CSe) |
| 3.18 (m, H$_3$) |
| 3.68 (s, OC$\underline{H}_3$) |
| 4.00 (d, J = 2Hz, H$_4$) |
| 4.27 (m, CH$_3$C$\underline{H}$OSi) |
| 6.05 (br.s, NH) |
| 7.32–7.67 (aromatic protons) |

IR (CH$_2$Cl$_2$) 3400 (NH), 1769 (β-lactam C=O), 1725 (ester C=O) cm$^{-1}$.

mp (recrd. hexane), 128°–130° C.

Anal. calcd. for C$_{21}$H$_{33}$NO$_4$SeSi: C, 53.60; H, 7.07; N, 2.98; Found: C, 53.68; H, 7.12; N, 2.91.

STEP B

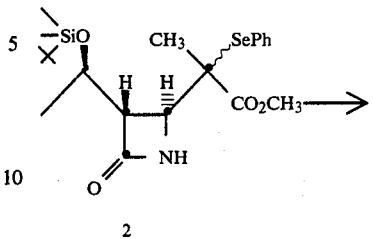

2

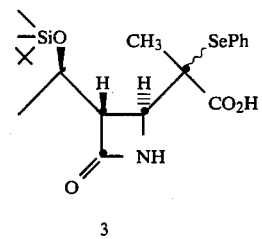

3

To a solution of the major diastereoisomer of 2 (0.89 g, 1.9 mmol) in 4:1 MeOH:H$_2$O (23 ml), 2.8N NaOH (1.6 ml, 4.5 mmol) is added, and the resultant mixture is heated at 60° C. under nitrogen for 2 hours. After cooling to room temperature, the reaction is poured into 2N HCl (5 ml)-H$_2$O (60 ml)-ethyl acetate (60 ml). After separation of the organic phase, the aqueous layer is again extracted with ethyl acetate (60 ml). The combined organic layers are washed with brine, dried over MgSO4, filtered, and concentrated in vacuo to give crude 3 (0.84 g). The crude material is dissolved in chloroform, treated with charcoal, and reconcentrated. Recrystallization of the material from ether provides 3 as white crystals (0.43 g, 50% yield). A second crop affords additional 3 (0.16 g, 19% yield).

Data for Product of Step B:

| NMR (CDCl$_3$, TMS); δ |
| --- |
| 0.02 & 0.06 [2 singlets, Si(CH$_3$)$_2$] |
| 0.86 [s, SiC(CH$_3$)$_3$] |
| 1.27 (d, C$\underline{H}_3$CHOSi) |
| 1.52 (s, C$\underline{H}_3$CSe) |
| 3.15 (m, H$_3$) |
| 4.17 (d, J = 2Hz, H$_4$) |
| 4.25 (m, CH$_3$CHOSi) |
| 6.31 (NH) |
| 7.31–7.76 (aromatic protons) |

IR (CH$_2$Cl$_2$) 1760 & 1740 (carbonyls) cm$^{-1}$ mp (recrd. ether), 172°–176° C.

Anal. Calcd. for C$_{20}$H$_{31}$NO$_4$SeSi: C, 52.62; H, 6.85; N, 3.07; Found: C, 52.77; H, 6.82; N, 2.93.

STEP C

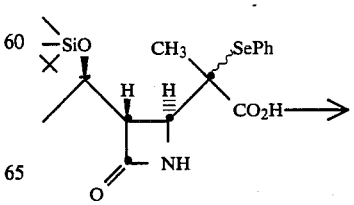

3

-continued
STEP C

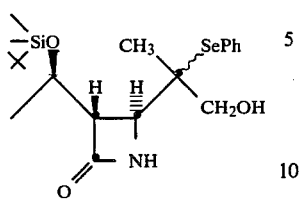

4

A 10M solution of borane-methylsulfide complex (0.38 ml, 3.8 mmol) is added to a solution of 3 (0.4 g, 0.88 mmol)) in anhydrous tetrahydrofuran at 0° C. under nitrogen. After 5 minutes the reaction mixture is allowed to stir at room temperature for 2.5 hours. After that time period, the reaction is cooled to 0° C. and methanol (4.6 ml) is carefully added to destroy the excess BH₃. After the initial evolution of hydrogen, the 0° C. bath is removed, and stirring is continued for 15 minutes. The reaction mixture is concentrated in vacuo without heat and then partitioned between methylene chloride and brine. The organic layer is separated, and the aqueous layer is again extracted with methylene chloride. The combined organic layers are dried over MgSO₄, filtered and concentrated in vacuo to give crude 4 (0.37 g). Preparative thin layer chromatography on silica gel (eluting with 20% ethyl acetate-methylene chloride and extracting with 10% methanol-methylene chloride) provides the alcohol, 4 (0.29 g, 75% yield).
Data for Product of Step C:

| NMR (CDCl₃, TMS); δ |
|---|
| 0.09 & 0.12 [2 singlets, Si(CH₃)₂] |
| 0.90 [s, SiC(CH₃)₃] |
| 1.26 (s, CH₃CSe) |
| 1.35 (d, C$\underline{H}$₃CHOSi) |
| 2.76 (dd, CH₂O$\underline{H}$) |
| 3.40 (m, H₃) |
| 3.66 (m, C$\underline{H}$₂OH) |
| 3.80 (d, J = 2Hz, H₄) |
| 4.22 (m, CH₃C$\underline{H}$OSi) |
| 5.64 (br.s, NH) |
| 7.32–7.74 (aromatic protons) |

IR (CH₂Cl₂) 1760 (β-lactam C=O) cm⁻¹.
mass spectrum (of diTMS derivative) 530 (MI-t-butyl)

STEP D

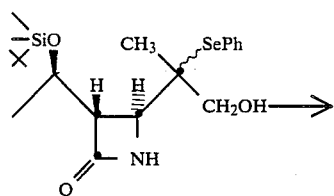

4

-continued
STEP D

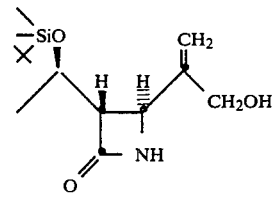

5

To a solution of 4 (0.29 g, 0.65 mmol) in tetrahydrofuran (3.3 ml) at 0° C., acetic acid (0.1 ml, 1.7 mmol) and 30% hydrogen peroxide (0.45 ml, 4.0 mmol) are added. After stirring at 0° C. for 5 hours, the reaction mixture is carefully added to cold saturated NaHCO₃ (10 ml) and ether (25 ml). After phase separation, the aqueous layer is again extracted with ether. The combined ether layers are then washed two times with brine, dried over MgSO₄, filtered and concentrated to vacuo to crude 5 (0.19 g). Preparative thin layer chromatography on silica gel (eluting with 20% ethylacetate-methylene chloride and extracting with 10% methanol-methylene chloride) provides 5 as a white crystalline product (0.14 g; 78% yield).
Data for Product of Step D:

| NMR (CDCl₃, TMS); δ |
|---|
| 0.13 [s, Si(CH₃)₂] |
| 0.91 [s, SiC(CH₃)₃] |
| 1.30 (d, C$\underline{H}$₃CHOSi) |
| 2.30 (m, CH₂O$\underline{H}$) |
| 3.05 (m, H₃) |
| 4.10–4.29 (m, H₄, C$\underline{H}$₂OH and CH₃C$\underline{H}$OSi) |
| 5.20 & 5.23 (2 br s, C$\underline{H}$₂=C) |
| 6.05 (br s, NH) |

IR(CH₂Cl₂) 1770 (β-lactam C=O) cm⁻¹.
mp-130°–133.5° C.
Anal. Calcd. for C₁₄H₂₇NO₃Si: C, 58.88; H, 9.53; N, 4.91; Found: C, 59.08; H, 9.76; N, 4.69.

STEP E

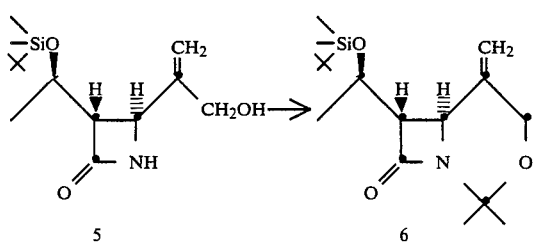

5         6

To a solution of 5 (134 mg, 0.47 m mol) in sieve-dried methylene chloride (3.6 ml) is added 2,2 dimethoxypropane (74 microl., 0.60 mmol) and BF₃·Et₂O- (6 microl.). After stirring at room temperature under nitrogen for 30 minutes, the reaction mixture is added to 1M K₂HPO₄ (2 ml)-brine (8 ml)-methylene chloride (10 ml). After phase separation, the aqueous layer is again extracted with methylene chloride (10 ml). The combined organic layers are washed two times with brine, dried over MgSO₄, filtered and concentrated in vacuo to give crude 6 (144 mg). Chromatography on a column of Baker's silica gel eluting with 0% to 2% ethyl acetate in methylene chloride provides purified 6 (139 mg, 91% yield).

Data for Product of Step E:

| NMR (CDCl₃, TMS); δ |
| --- |
| 0.07 & 0.08 [2 singlets, Si(CH₃)₂] |
| 0.88 [s, SiC(CH₃)₃] |
| 1.25 (d, CH₃CHOSi) |
| 1.44 & 1.71 [2 singlets, (CH₃)₂C] |
| 3.04 (dd, J = 2 & 4Hz, H₇) |
| 4.16–4.34 (m, H₆, CH₃CHOSi, & CH₂O) |
| 4.96 & 5.08 (2 br S, CH₂=C) |

IR (CH₂Cl₂) 1750 (β-Lactam C=O) cm⁻¹.
mp 46°–48° C.
M.S. 268 (MI-t-butyl), 166 (MI-CH₃CHOtBDMSi).

STEP F

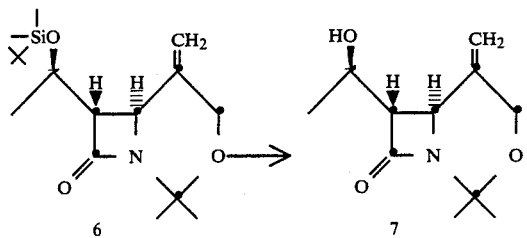

To a solution of 6 (67 mg, 0.21 mmol) in anhydrous dimethylformamide at 0° C. under nitrogen is added 1M tetrabutylammonium fluoride in tetrahydrofuran (0.31 ml, 0.31 mmole), and stirring is continued for 1 hour at room temperature. The reaction mixture is added to saturated aqueous ammonium chloride (20 ml) and ether (20 ml). After phase separation, the aqueous phase is again extracted with ether (20 ml). The combined ether layers are washed two times with brine, dried, filtered and concentrated in vacuo to give crude 7 (31 mg). Chromatography on a small column of Baker's silica gel, eluting with 0% to 50% ethyl acetate in methylene chloride, provides purified 7 (26 mg, 60% yield).

Data for Product of Step F:

| NMR (CDCl₃, TMS); δ |
| --- |
| 1.33 (d, J = 6Hz, CH₃CHOH) |
| 1.47 & 1.73 (2 singlets, (CH₃)₂C) |
| 2.62 (br, OH) |
| 3.08 (dd, J = 2 & 5Hz, H₇) |
| 4.22 (m, H₆, CH₃CHOH, & CH₂O) |
| 5.05 (center of m, CH₂=C) |

IR (CH₂Cl₂) 3650 (OH), 1746 (C=O) cm⁻¹.

STEP G

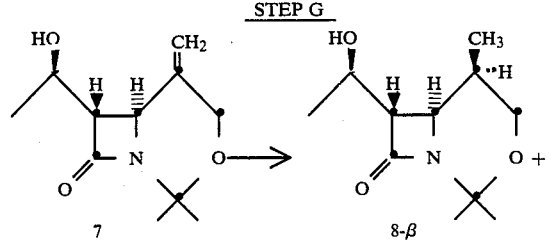

-continued
STEP G

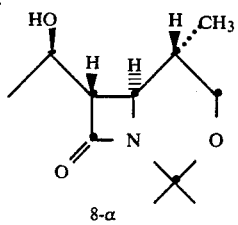

8-α

Raney Nickel, commercially obtained from W. R. Grace Co., as Grace No. 28 Type Raney Nickel (W-4), is washed repeatedly with water until the supernatant is neutral and then 5 times with ethanol. Six drops of this Raney Nickel slurry in ethanol is added to 7 (5 mg; 0.024 mmol) in ethanol (0.3 ml). The reaction mixture is shaken on a Parr apparatus at room temperature under 40 p.s.i.g. H₂ for 2.5 hour. The reaction mixture is then filtered through Celite, rinsing in with ethyl acetate. The filtrate is concentrated in vacuo and applied in methylene chloride to a small column of Baker's silica gel, eluting first with 100% methylene chloride and then 75% ethyl acetate in methylene chloride. The product isolated (4.8 mg, 94% yield) contains a mixture of 8β and 8α in a molar ratio of 9:1 as approximated by 300 mHz NMR analysis.

Data for Products of Step G:

| NMR (CDCl₃, TMS); δ |
| --- |
| 0.91 (d, α-CH₃) |
| 1.12 (d, β-CH₃) |
| 1.30 (d, CH₃CHOH of 8β) |
| 1.31 (d, CH₃CHOH of 8α) |
| 1.42 & 1.74 (2 singlets, (CH₃)₂C of 8β) |
| 1.41 & 1.75 (2 singlets, (CH₃)₂C of 8α) |
| 1.87 (d, OH) |
| 1.96 (m, H₅) |
| 2.83 (dd, J = 2 & 5.5Hz, H₇ of 8α) |
| 3.06 (dd, J = 2 & 6Hz, H₇ of 8β) |
| 3.18 (dd, J = 2 & 10Hz, H₆ of 8α) |
| 3.46 (t, J₄,₄ = J₄,₅ = 12Hz, H₄ of 8α) |
| 3.60 (dd, J₄,₄ = 12Hz, J₄,₅ = 3Hz, H₄ of 8β) |
| 3.73 (dd, J₄,₄ = 12Hz, J₄,₅ = 4.5Hz, H₄ of 8α) |
| 3.80 (dd, J = 2 & 5Hz, H₆ of 8β) |
| 3.98 (dd, J₄,₄ = 12Hz, J₄,₅ = 2Hz, H₄ of 8β) |
| 4.16 (m, CH₃CHOH) |

MS (of TMS derivative) 285 (MI), 270 (MI-CH₃).

What is claimed is:

1. A compound of the formula:

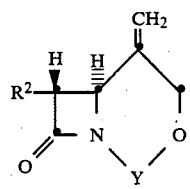

wherein R² is independently selected from hydrogen, linear or branched C₁-C₃ alkyl, which can be substituted with fluoro, hydroxy or protected hydroxy, and Y is a divalent bridging-protecting group, derived from a ketone, aldehyde or organosilicon compound, said group being stable to catalytic hydrogenation and removable by acid or base hydrolysis.

2. The compound of claim 1 wherein R² is independently selected from H, CH₃—, CH₃CH₂—, (CH$_3$)$_2$CH—, HOCH$_2$—, CH$_3$CHOH—, CH$_3$CH$_2$CHOH—, (CH$_3$)$_2$COH—, FCH$_2$CHOH—, FCH$_2$—, F$_2$CH—, F$_3$C—, CH$_3$CHF—, CH$_3$CF$_2$—, (CH$_3$)$_2$CF— or CH$_3$CH[OSi[C(CH$_3$)$_3$](CH$_3$)$_2$].

3. The compound of claim 1 wherein said Y is selected from (CH$_3$)$_2$C<,

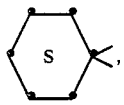

(t-Bu)$_2$Si<, or

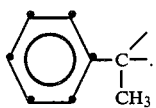

4. The compound of claim 2 being of the structural formula:

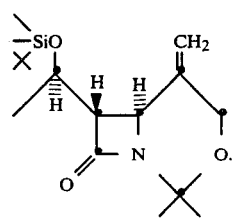

5. The compound of claim 2 being of the structural formula:

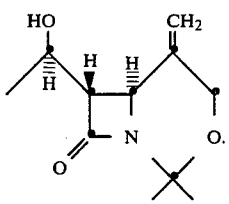

6. The compound of claim 1 being of the formula:

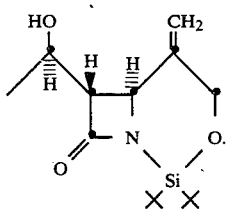

* * * * *